United States Patent [19]

Sawaya

[11] Patent Number: 5,176,256
[45] Date of Patent: Jan. 5, 1993

[54] CONTAINER FOR USED MEDICAL INSTRUMENTS

[76] Inventor: Frederick J. Sawaya, 5631 Farmington Rd., West Bloomfield, Mich. 48322

[21] Appl. No.: 790,041

[22] Filed: Nov. 12, 1991

[51] Int. Cl.⁵ ............................... B65D 83/10
[52] U.S. Cl. ................... 206/366; 220/908; 220/254; 220/255; 220/259
[58] Field of Search ............ 206/365, 366, 363; 220/908, 910, 254, 255, 256, 259, 334, 333

[56] References Cited

U.S. PATENT DOCUMENTS

| | | | |
|---|---|---|---|
| 1,365,558 | 1/1921 | Sokolowski | 220/255 |
| 1,763,907 | 6/1930 | Sommers | 220/255 |
| 2,054,145 | 9/1936 | Tandy | 220/259 X |
| 2,413,923 | 1/1947 | Kackley et al. | 220/255 X |
| 4,576,281 | 3/1986 | Kirksey | 206/366 X |
| 4,809,850 | 3/1989 | Laible et al. | 206/366 |
| 4,890,733 | 1/1990 | Anderson | 206/366 X |
| 4,903,832 | 2/1990 | Stewart | 206/366 |
| 4,930,631 | 6/1990 | Bruno | 206/366 |
| 5,014,874 | 5/1991 | Kitsos et al. | 206/366 X |
| 5,080,251 | 1/1992 | Noack | 206/366 X |

*Primary Examiner*—Steven N. Meyers
*Assistant Examiner*—Jacob K. Ackun, Jr.
*Attorney, Agent, or Firm*—Dykema Gossett

[57] ABSTRACT

Two containers for storing soiled medical instruments are disclosed. In one container an elongate cylindrical body has an entrance door through its cylindrical wall, and a pivotable end cap. Soiled medical instruments can be inserted through the door, or through the end cap. In a second embodiment, a case has an entrance door at one end which allows medical instruments to be moved into the interior of the case. A safety door spaced within the case from the entrance door ensures that medical personnel are not exposed to previously stored instruments while inserting additional instruments into the case.

7 Claims, 3 Drawing Sheets

CONTAINER FOR USED MEDICAL INSTRUMENTS

BACKGROUND OF THE INVENTION

This invention relates to containers for storing soiled sharp medical instruments.

Recently containers have been developed to allow the storage of soiled sharp medical instruments during medical procedures. During a medical operation a number of sharp medical instruments such as used or soiled syringes or needles must be disposed. It is important to ensure that medical personnel are not cut by the soiled sharp medical instruments, as they may become exposed to diseases carried on the instruments.

While the prior art containers have beneficial characteristics, it would be desirable to improve upon the protection afforded by the prior art containers, to improve the ease of access and storage of these containers, and further to improve upon the ease of use of these containers to receive and store soiled sharp medical instruments.

SUMMARY OF THE INVENTION

In a first embodiment of the present invention a generally cylindrical elongate container includes a door extending through a cylindrical wall. Long sharp medical instruments may be inserted through the door, and into the interior of the container. One end of the container includes a foam base which receives the sharp medical instruments. An opposed end of the container is hingedly attached to the cylindrical body, and pivots away from the body to provide access to the interior of the container for disposal of smaller sharp medical instruments. Preferably, the door through the cylindrical wall of the container is formed of two door halves, with an inner door half abutting an inner face of an outer door half. The inner door half pivots inwardly of the body of the container when a sharp medical instrument is inserted into the container. Most preferably the entire interior of the container is lined with a cotton-like material.

In a second embodiment of the present invention, a container body is generally box-like in construction, and has an entrance door through one end face. A safety door is spaced inwardly of the body from the entrance door. The entrance door is pivotable between a position blocking access to the interior of the container and an open position where sharp medical instruments can be inserted into the interior. The safety door pivots with the entrance door such that all sharp medical instruments fall into the container, beyond the entrance door and the safety door into a space beneath the safety door for storage. This provides a subcompartment within the container body between the entrance door and safety door which contains no soiled medical instruments. This subcompartment ensures that medical personnel are not exposed to previously stored instruments when they are inserting additional sharp medical instruments into the container body.

Pins connect the entrance and safety doors to pivot together, and a cylinder biases the safety door to a closed position. As the safety door is biased to the closed position it in turn biases the entrance door to a closed position. The entrance door is positioned within an end face, and underneath a fixed end wall at a portion of the lateral extend of the body that the entrance door does not extend beyond. The fixed end wall covers and protects the edge of the entrance door such that medical personnel are not exposed to soiled medical instruments within the container when inserting an additional instrument. Preferably, the safety door is spaced from the entrance door by a distance which is less than half the height of the container.

Hooks are preferably positioned on the body adjacent to the entrance door such that the entire body can be hung upon a rail, or similar structure, for easy access to medical personnel. The body is preferably formed of two halves which pivot away from each other to allow access to the entire interior of the body such that the soiled medical instruments can be disposed of, and the body reused.

These and other features and objects of the present invention can be best understood from the following specification and drawings, of which the following is a brief description.

DETAILED DESCRIPTION OF A PREFERRED EMBODIMENT

Figure 1:
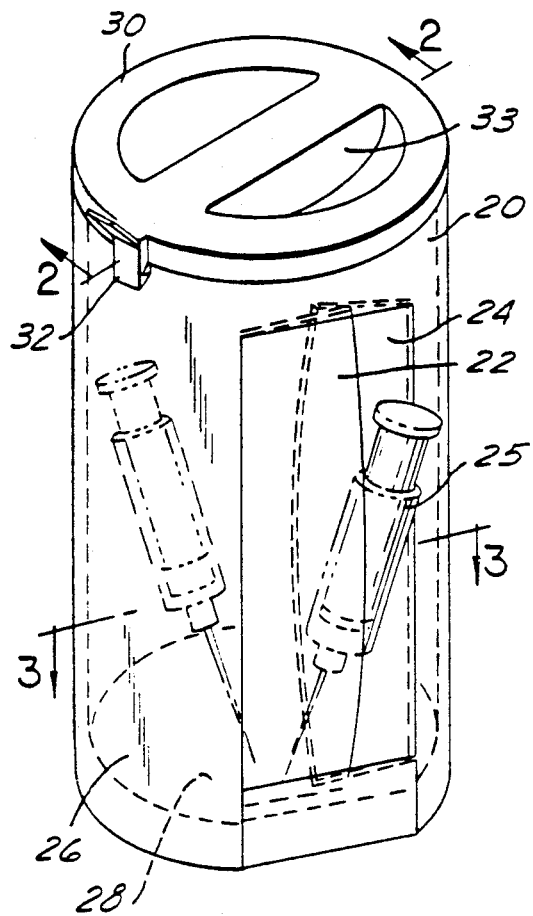
FIG. 1 is a perspective view of a first embodiment of the container for disposing of sharp medical instruments.

A first embodiment container 20 is shown in FIG. 1 which is generally formed of an elongate cylindrical body. An outer door half 22 extends through the cylindrical wall, and mates with a second door half 24. Syringe 25 is shown being inserted through door half 24 into interior 26 of the container. Outer door half 22 overlaps inner door half 24 to block access to interior 26 of the container body. Foam pad 28 is positioned at one end of the cylindrical body 20. A pivoting lid 30 is positioned at the opposed end, with a latch 32 normally securing lid 30 on cylindrical body 20. Handle 33 facilitates pivoting of lid 30 and carrying of container 20.

Figure 2:
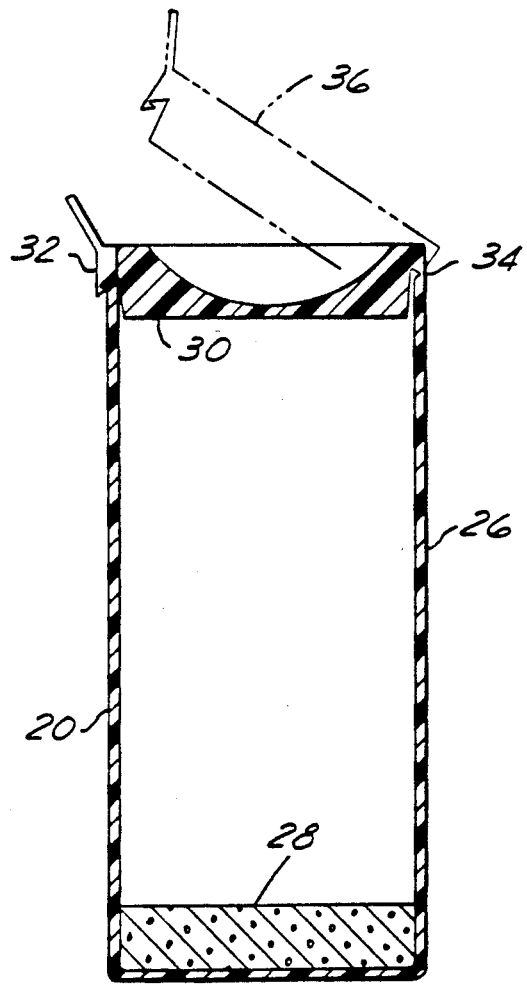
FIG. 2 is a cross-sectional view taken along line 2—2 as shown in FIG. 1.

As shown in FIG. 2 lid 30 pivots on hinge 34 to an open position 36 shown in phantom. Smaller soiled medical instruments, such as needles, are inserted through the open end into the interior 26 of body 20. The small soiled medical instruments can be inserted into the foam pad 28.

Figure 3:
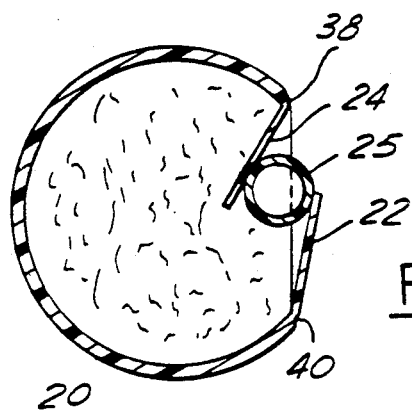
FIG. 3 is a cross-sectional view taken along line 3—3 as shown in FIG. 1.

As shown in FIG. 3, long sharp medical instruments such as syringe 25 are forced against inner door half 24, such that inner door half 24 pivots on a living hinge 38, outer door half 22 may pivot slightly outwardly on living hinge 40. Syringe 25 may then move into the interior 26 of container 20.

Figure 4:
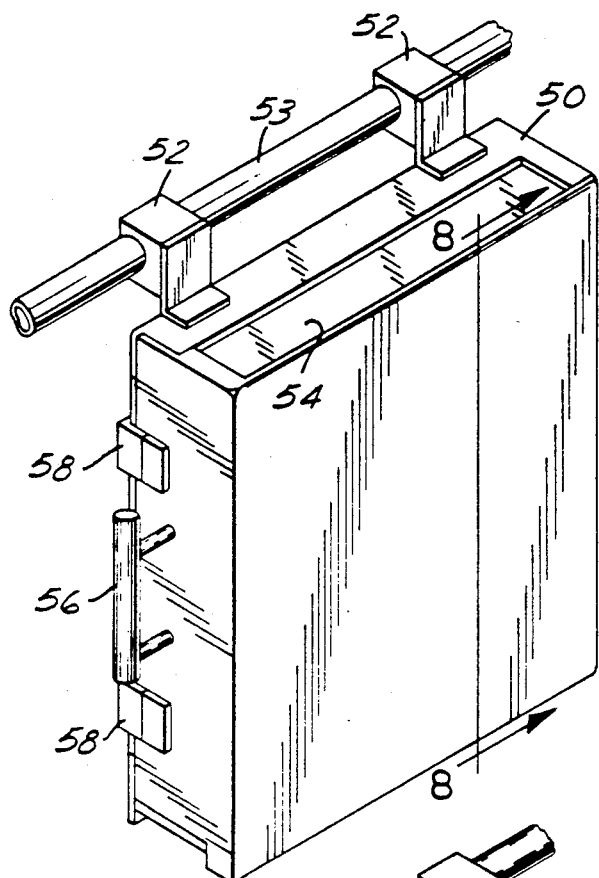
FIG. 4 is a perspective view of a second embodiment of the container for storing soiled medical instruments.

A second embodiment container 50 is shown in FIG. 4. Second embodiment container 50 is generally in the shape of a rectangular case, and has hooks 52 which are mounted on rod 53 or similar structure. Rod 53 may be a rail on a hospital bed, or may be mounted within any type of medical environment, such as an operating room. An entrance door 54 at one end of the body of container 50 allows access to the interior of the body. A handle 56, and latches 58 allow container 50 to be easily transported and opened for emptying and disposal of soiled medical instruments.

Container 50 could be said to have a longitudinal dimension, shown here as the vertical dimension, a lateral dimension, shown here being parallel to a rail 53, and a depth, to define its three-dimensional shape. Entrance door 54 extends through an end face defined by its depth and lateral extent.

Figure 5:
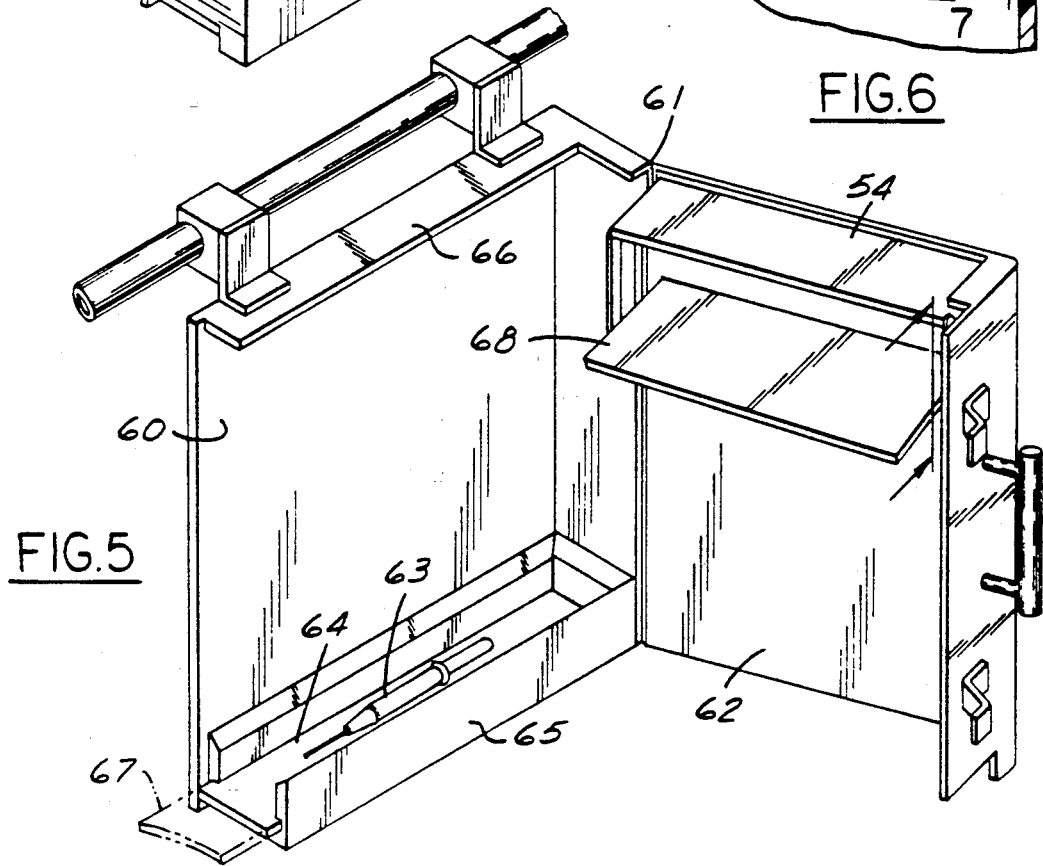
FIG. 5 is a perspective view showing the second embodiment of the container in an open position.

As shown in FIG. 5, container 50 consists of a pair of body halves 60 and 62 which pivot on hinge 61 to an open position to allow removal of soiled medical instruments 63 from a base 64. Ledge 65 forms a storage area with base 64. Fixed end wall 66 cooperates with an edge of entrance door 54 to ensure that medical personnel are not exposed to sharp medical instruments stored within container 50. Cotton or absorbent material or pad 67 is placed on base 64 to absorb any blood or fluids. A safety door 68 is spaced longitudinally inwardly of entrance door 54, and further protects medical personnel from any soiled medical instruments stored within container 50. Safety door 68 is located in a top half of container 50, and is spaced by less than half of the longitudinal distance from entrance door 54. This maximizes the storage potential of container 50.

Figure 6:
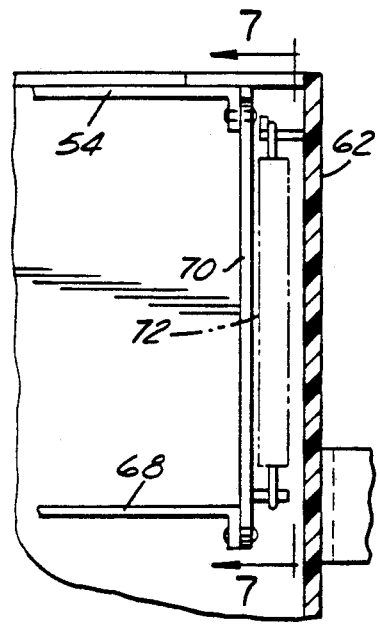
FIG. 6 is a cross-sectional view taken along line 6—6 as shown in FIG. 5.

As shown in FIG. 6, a pin 70 connects safety door 68 and entrance door 54, such that when entrance door 54 is pivoted open it pivots safety door 68 open. A spring 72 is fixed to body 62 and safety door 68, and biases safety door 68 back to a closed position relative to container 50, which in turn biases entrance door 54 back to a closed position.

Figure 7:
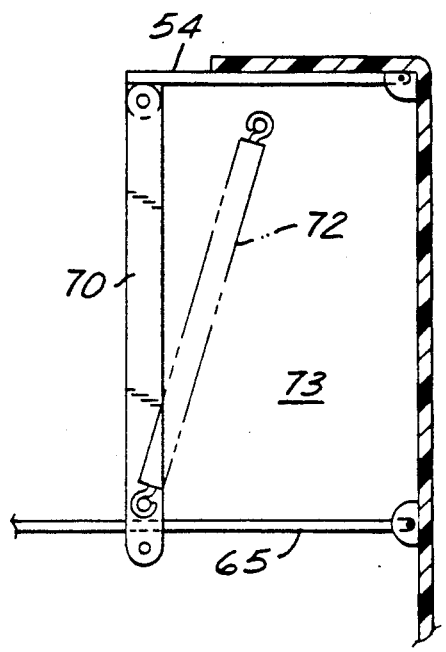
FIG. 7 is a cross-sectional view taken along line 7—7 as shown in FIG. 6.

As shown in FIG. 7, entrance door 54 is connected by pin 70 to safety door 68. Spring 72 is fixed to container 50, and biases safety door 68, and entrance door 54 to a closed position.

Figure 8:
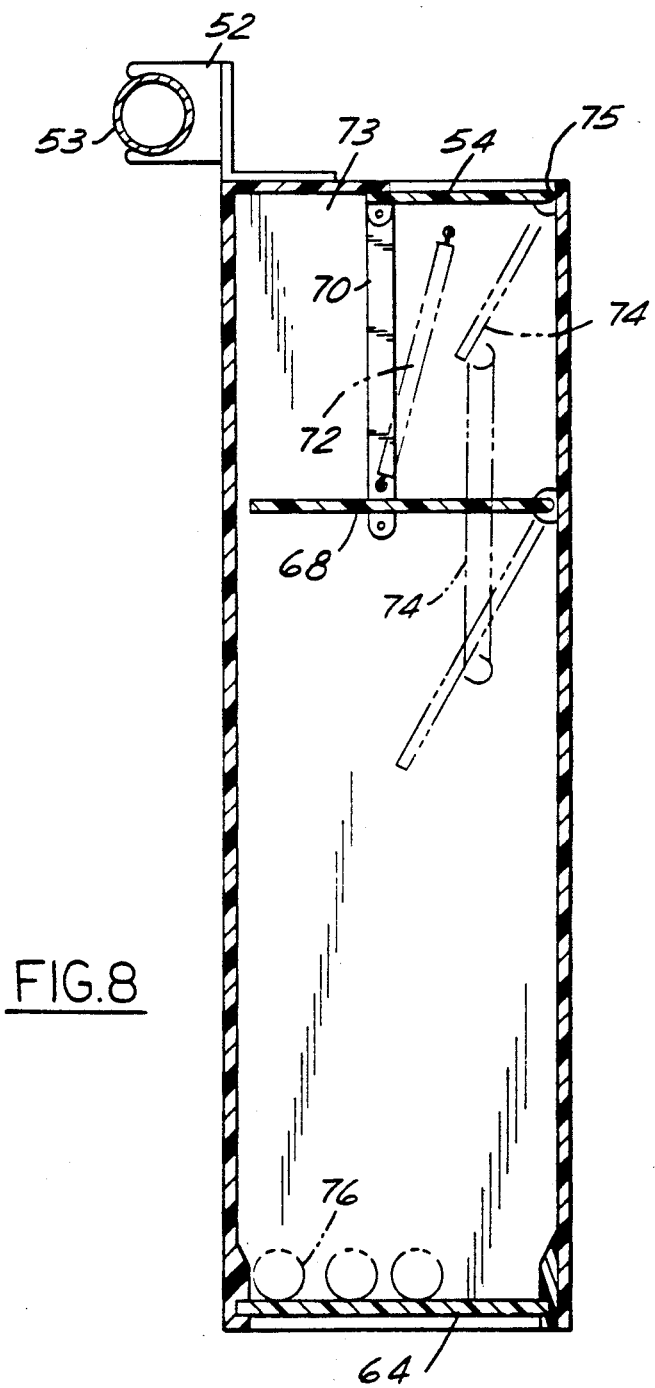
FIG. 8 is a cross-sectional view taken along line 8—8 as shown in FIG. 4.

As shown in FIG. 8, safety door 68 extends over the majority of the depth of container 50. Entrance door 54 is biased against an inner face of fixed end wall 66. Access to the interior of container 50 is blocked by fixed end wall 66, since the edge of entrance door 54 abuts fixed wall 66. Safety door 68 is positioned inwardly of entrance door 54, to form a subcompartment 73. Should entrance door 54 be slightly opened, subcompartment 73 and safety door 68 will prevent medical personnel from exposure to soiled medical instruments 76 within container 50.

When a soiled medical instrument is inserted, entrance door 54 is pivoted on hinge 75 to the open position 74, as shown in phantom. Pins 70 cause safety door 68 to pivot to an open position, and soiled medical instruments 76 fall to the bottom or base 64 of container 50. Subcompartment 73 remains free of any soiled instruments. Once soiled medical instruments 76 have filled the space within container 50, safety door 68 will no longer be able to pivot open, but instead will contact previously stored medical instruments. At that time, an operator will understand that it is time to remove container 50 from its storage position, open the two halves and remove all soiled medical instruments 76. Container 50 may then be reused.

Preferred embodiments of the present invention have been disclosed, however, a worker of ordinary skill in the art would recognize that certain modifications would come within the scope of this invention. For that reason the following claims should be studied in order to determine the true scope and content of this invention.

I claim:

1. A container for storing used sharp medical instruments comprising:
   a body defining a space within said body for storage of medical instruments;
   an entrance opening extending through said body and an entrance door selectively closing said entrance opening such that medical instruments can be inserted through said entrance door and into said space, said entrance door being pivotally attached to said body such that said entrance door pivots inwardly between a closed position where it blocks access to the interior of said body, and an open position where it allows access to the interior of said body such that medical instruments may be inserted into said body;
   a safety door spaced inwardly of said body from said entrance door, inward pivoting of said entrance door as said entrance door moves between said closed and open positions causing said safety door to pivot inwardly;
   said body having a depth, a lateral dimension and a longitudinal dimension, and said entrance door is defined in an outer end face of said body defined by said depth and said lateral dimensions, said entrance door being received on a longitudinally inner wall of said outer end face in said closed position, said safety door being spaced longitudinally inwardly from said entrance door, and said safety door extending across the majority of said depth and lateral dimension of said body to define a subcompartment within said body when said safety door and said entrance door are in said closed position;
   at least one pin interconnecting said entrance door and said safety door such that pivoting movement of said entrance door causes pivoting movement of said safety door;
   said entrance door not extending across the entire extent of said body, and positioned inwardly of said fixed outer end face of said body, said entrance door extending for a greater dimension than said entrance opening, such that a part of said door abuts said inner wall, said entrance door being pivotable away from said fixed end wall into the interior of said body, said fixed end wall blocking access to the interior of said body when said entrance door is in said closed position; and
   a bias force maintaining said entrance door in said closed position.

2. A container as recited in claim 1, wherein said safety door is spaced from said entrance door by less than half of the longitudinal dimension.

3. A container as recited in claim 2, wherein a spring is fixed to an interior wall of said body at one end and fixed to said safety door at a second end, said spring biasing said safety door to said closed position, which in turn biases said entrance door to said closed position.

4. A container as recited in claim 1, wherein said body has a handle for transport.

5. A container as recited in claim 1, wherein said body is generally in the shape of a briefcase and has two halves which are latched together to close said body.

and said two halves of said body being openable to allow removal of soiled medical instruments within said body.

6. A container as recited in claim 5, wherein means to hang said body are positioned adjacent to said entrance door such that said body may be hung in a medical facility.

7. A container as recited in claim 5, wherein a ledge forms a storage compartment at the bottom of one of said halves.

* * * * *